United States Patent [19]

Yamada et al.

[11] Patent Number: 4,498,968
[45] Date of Patent: Feb. 12, 1985

[54] OXYGEN SENSOR

[75] Inventors: Tetsusyo Yamada; Yutaka Nakayama, both of Nagoya, Japan

[73] Assignee: NGK Spark Plug Co., Ltd., Nagoya, Japan

[21] Appl. No.: 525,701

[22] Filed: Aug. 23, 1983

[30] Foreign Application Priority Data

Mar. 29, 1983 [JP] Japan ................ 58-53164

[51] Int. Cl.³ ............................................ G01N 27/58
[52] U.S. Cl. .................................. 204/412; 204/425; 204/426
[58] Field of Search ............... 204/409, 410, 411, 424, 204/412, 425, 426; 123/438, 489; 60/276

[56] References Cited

U.S. PATENT DOCUMENTS

| | | | |
|---|---|---|---|
| 3,650,934 | 3/1972 | Hickam et al. | 204/412 |
| 4,272,329 | 6/1981 | Hetrick et al. | 204/412 X |
| 4,272,330 | 6/1981 | Hetrick | 204/426 X |
| 4,272,331 | 6/1981 | Hetrick | 204/412 X |
| 4,304,652 | 12/1981 | Chiba et al. | 204/426 X |
| 4,305,803 | 12/1981 | Beyer et al. | 204/429 X |
| 4,391,691 | 7/1983 | Linder et al. | 204/412 X |
| 4,394,222 | 7/1983 | Rohr | 204/412 X |

Primary Examiner—G. L. Kaplan
Assistant Examiner—Nam X. Nguyen
Attorney, Agent, or Firm—Fleit, Jacobson, Cohn & Price

[57] ABSTRACT

The disclosed oxygen sensor has a plate-like oxygen pump element with electrodes, a plate-like oxygen concentration cell element with electrodes, a means to couple the two elements in parallel to each other while forming a gap between those electrodes of the two elements which face with each other, and an oxygen diffusion resistive layer deposited on that electrode of the pump element which faces said gap, whereby said pump element pumps out oxygen from said gap so as to produce such an oxygen partial pressure in the gap under the presence of said oxygen diffusion resistive layer that the oxygen concentration of a gas surrounding the oxygen sensor is detected by coaction of said two elements.

12 Claims, 9 Drawing Figures

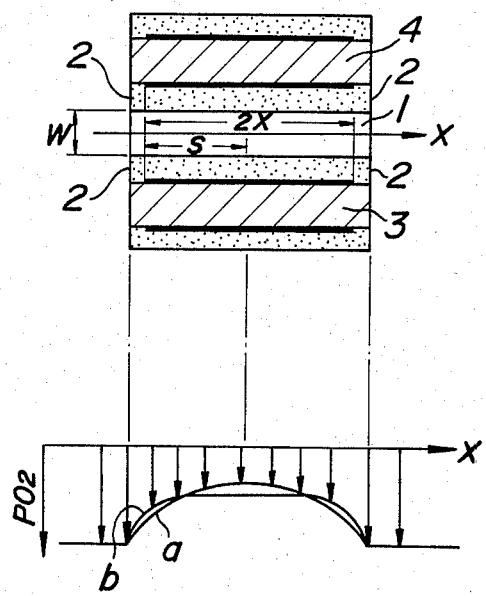
FIG.3A
FIG.3B
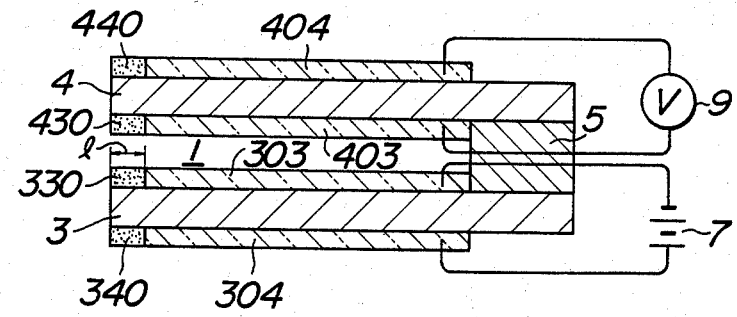
FIG.4

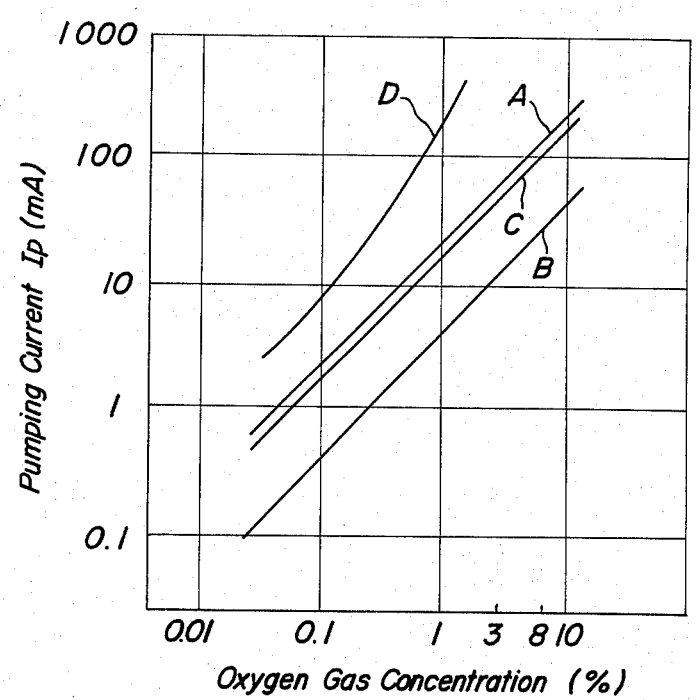
FIG_5

OXYGEN SENSOR

BACKGROUND OF THE INVENTION

1. Field of the Invention

This invention relates to an oxygen sensor, and more particularly to an oxygen concentration sensor using an active element made of an oxygen-ion-conductive solid electrolyte which is suitable for measuring oxygen concentration of an exhaust gas from a fuel combustion device such as an internal combustion engine, so as to facilitate control of air-fuel ratio of the fuel combustion device.

2. Description of the Prior Art

To simultaneously achieve fuel saving and exhaust gas purification in an internal combustion engine at least during regular running thereof, it has been proposed to burn fuel with an excess air by using a dilute mixture, for example, having an air-fuel ratio λ of about 1.4. To facilitate feedback control of this type fuel burning, there is a pressing need for such a durable oxygen sensor which maintains a good linearity of its output for oxygen concentrations of a desired range with a quick response and also maintains its performance over a long period of its service life.

There are oxygen sensors used for this purpose. One example of the oxygen sensors of the prior art for this purpose comprises a sintered wall member of an oxygen-ion-conductive solid electrolyte, such as stabilized or partially stabilized zirconia, and porous metallic layer electrodes deposited on opposite surfaces of the wall member, so as to form an active element capable of acting as an oxygen concentration cell element (a sensor element) or an oxygen pump element. In the case of the oxygen sensor using the active element as an oxygen pump element, a limiter member adapted to limit input and/or output flow of diffusing oxygen is included, so as to effect oxygen gas suction toward a suction side electrode of the pump element from the gas being measured, which gas surrounds the outside of the oxygen sensor. Two types of the limiter members are known; namely, a wall member covering the oxygen suction side electrode (minus side electrode) of the pump element so as to form a substantially enclosed chamber in cooperation with the pump element, the wall member having fine holes for limiting the oxygen diffusing into the enclosed chamber, and a porous layer member being in contact with the oxygen suction side electrode of the pump element so as to cover such electrode. The desired oxygen concentration of the gas being measured is determined by either of the two methods; namely, one method in which the corresponding relation between the desired oxygen concentration and a marginal oxygen inflow capable of passing through the above-mentioned limiter member is used and the marginal oxygen inflow is measured by using the value of a marginal pump current of the pump element, and another method which uses the relationship among the desired oxygen concentration of the gas being measured, the value of the pump current (the value of the pump current corresponds to the amount of diffusing oxygen inflow through the above-mentioned diffusion limiter member), and the counter electromotive force induced across the two electrodes of the pump element mainly in response to the oxygen partial pressure ratio therebetween at that moment.

Japanese Patent Laid-open Publication No. 130,649/1981 disclosed another example of the oxygen sensor of the prior art which uses a substantially enclosed chamber having a hole. The cross-sectional area of the hole of the chamber is small as compared with the size of the chamber, so that the hole acts as a localized choke, and it is intended to limit the oxygen diffusion substantially only to a path through such hole. In fact, the total cross-sectional area of the hole is small, for instance, less than 1 $mm^2$. This type oxygen sensor of the prior art has shortcomings in that its response for sudden change of oxygen concentration is slow due to the smallness of the hole, and that the operating characteristics of the oxygen sensor is apt to change during a long period of running due to deposition of combustion by-products of liquid fuel.

In the case of the oxygen sensor using a porous layer as an oxygen diffusion limiter member, it is rather difficult to make such porous layer in a stable fashion in the form of a comparatively thin layer having a strong diffusion limiting ability by using a metallic material or metal oxide material. The operating characteristics of this type oxygen sensor is also apt to change during a long period of running due to deposition of combustion by-products.

SUMMARY OF THE INVENTION

An object of the present invention is to obviate the above-mentioned shortcomings of the prior art by providing an improved oxygen sensor.

Another object of the invention is to provide an oxygen sensor having a novel oxygen diffusion resistive layer which is based on a completely different operative mechanism from that of the conventional diffusion limiter members, whereby the shortcomings of the prior art are obviated.

To fulfil the above-mentioned objects, an oxygen sensor according to the present invention comprises an oxygen pump element having a first oxygen-ion-conductive solid electrolyte board with electrode layers attached to opposite surface at one end of the first board, and an oxygen concentration cell element having a second oxygen-ion-conductive solid electrolyte board with electrode layers attached to opposite surfaces at one end of the second board. A means couples said oxygen pump element and said oxygen concentration cell element in parallel to each other with a gap between the electrode layers attached to the opposing surfaces of the first board and the second board. The electrode of the oxygen pump element on the side facing the gap is porous. At least one oxygen diffusion resistive layer is deposited on that electrode layer of the oxygen pump element which faces the gap. Whereby, the oxygen pump element transfers oxygen between the gap and outside of the oxygen sensor by a small electric current therethrough under the presence of the oxygen diffusion resistive layer so as to produce such an oxygen concentration differential between the gap and the outside of the oxygen sensor that the oxygen concentration cell element generates an electromotive force in response to the oxygen concentration differential. The oxygen concentration at the outside of the oxygen sensor is determined by a combination of the electric current and the electromotive force.

The inventors confirmed through tests that the oxygen sensor of the invention has substantially linear output characteristics over a wide range of oxygen concentration in a gas being measured, from a low concentration to a high concentration, while consuming only a little power, and that the response of its output for sudden change in the oxygen concentration is excellent.

BRIEF DESCRIPTION OF THE DRAWINGS

For a better understanding of the invention, reference is made to the accompanying drawings, in which:

FIG. 3A is a schematic sectional view of the oxygen sensor as seen from the direction of the arrows III, III of FIG. 2;

FIG. 3B is an explanatory diagram showing the distribution of oxygen gas concentration in a gap of the oxygen sensor;

FIG. 4 is a schematic sectional view of another oxygen sensor according to the present invention;

FIG. 5 is a graph showing the result of tests which were carried out on Specimens of the oxygen sensor according to the present invention.

Throughout different views of the drawings, 1 is a flat gap, 2 is an open edge, 3 is a first solid electrolyte board, 301 and 302 are electrode layers, 310 and 320 are porous electrode-covering layers, 4 is a second solid electrolyte board, 401 and 402 are electrode layers, 410 and 420 are electrode-covering layers, 5 is a connecting member, 6 is a lead wire, and 7 is an electric power source.

DESCRIPTION OF THE PREFERRED EMBODIMENTS

Figure 1:
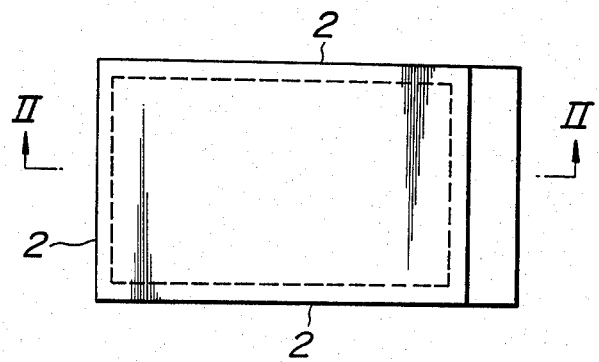
FIG. 1 is a schematic plan view of an oxygen sensor according to the present invention.
Figure 2:
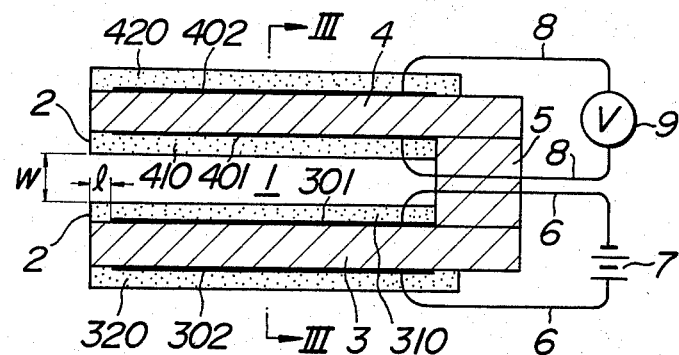
FIG. 2 is a schematic sectional view of the oxygen sensor as seen from the direction of the arrows II, II of FIG. 1.

Referring to a first embodiment as shown in FIGS. 1, 2 and 3A, an oxygen sensor of the present invention has a flat gap 1 with a spacing W between opposite ends thereof, which gap is exposed to a gas to be measured. The flat gap 1 has slit-like openings or open edges 2 extending along the periphery of the flat gap 1. It is an important feature of the invention that the open edge 2 is substantially free from the oxygen diffusion resistance which is to be explained hereinafter, or the open edge 2 does not cause any excessively localized restriction of the oxygen diffusion.

A first solid electrolyte board 3 disposed on one side of the flat gap 1 is the solid electrolyte board of an oxygen pump element. A very thin porous electrode 301 made of heat resistive metal is deposited on that portion of the first board 3 which faces the flat gap 1, by a suitable thin film forming method such as evaporation or plating. The thickness of the porous electrode 301 is 1 μm or less. A porous electrode-covering layer 310 is deposited on the surface carrying the electrode 301 by a suitable thick film forming method. Major ingredient of the electrode-covering layer 310 is ceramic material. In this first embodiment, the combination of the electrode layer 301 and the electrode-covering layer 310 forms a layer which is resistive against diffusion of oxygen gas (to be referred to as the oxygen diffusion resistive layer, hereinafter). The formation of the oxygen diffusion resistive layer is not limited to such combination, and a composite single layer capable of acting as an oxygen diffusion resistive layer can be overlaid on the solid electrolyte board.

That surface of the first solid electrolyte board 3 which is opposite to the flat gap 1 may be provided with a thin porous metallic electrode layer 302 alone, which can be deposited by a thin film forming method such as evaporation or plating. As shown in the figure, it is more preferable to deposit a combination of the electrode layer 302 and an electrode-covering layer 320 in a manner similar to that of the surface facing the flat gap 1. Whereby, the surface opposite to the flat gap 1 is provided with an oxygen diffusion resistive layer which also acts as a protective layer of the electrode layer 302 against thermal shock.

A second solid electrolyte board 4 disposed on the other side of the flat gap 1 is the solid electrolyte board of an oxygen concentration cell element. A very thin porous electrode layer 401 made of heat resistive metal is deposited on that portion of the second board 4 which faces the flat gap 1, by a suitable thin film forming method such as evaporation or plating. The porous electrode layer 401 may be provided only at a comparatively small portion of the surface of the second board 4 including a portion facing the central part of the flat gap 1. From the standpoint of quick response to sudden change of oxygen concentration, it is preferable to spread the electrode layer 401 over the major portion of the gap facing surface of the second board 4, and in this case, it is also preferable to dispose an oxygen diffusion resistive layer similar to that of the oxygen pump element on the oxygen concentration cell element so as to ensure a high sensitivity. Accordingly, the second solid electrolyte board 4 of the illustrated embodiment is processed in a manner similar to that of the first solid electrolyte board 3, i.e., a combination of the thin heat resistivity metallic electrode layer 401 and a comparatively thick ceramics-rich porous electrode-covering layer 410 and another combination of a thin heat resistive metallic electrode layer 402 and a comparatively thick ceramics-rich porous electrode-covering layer 420 are deposited on opposite surfaces of the second board 4 in alignment with the flat gap 1.

A connecting means 5 integrally joins the substantially parallel boards 3 and 4 at the opposite ends to the flat gap 1, so as to maintain the constant spacing W at the gap 1. For instance, the connecting means 5 can be formed by using a suitable adhesive.

Preferably, setbacks are taken at the fringes of the electrodes 301 and 302 deposited on the opposite surfaces of the first board 3 of the oxygen pump element. The setbacks are formed along the open edge 2 of the flat gap 1 by setting back the fringe of the electrodes 301 and 302 from the open edge 2 by a distance of l. However, such setbacks can be dispensed with if so desired. The magnitude of the spacing W of the gap 1 must be very small as compared with the area Z of the porous electrode 301 and 302, so that the gap 1 is flat. As compared with an oxygen-diffusion-restricting zone depth S in the gap 1 which will be described hereinafter, the spacing W of the gap 1 should preferably be less than 13% of such depth S ($W/S < 0.13$), more preferably less than 10% thereof ($W/S < 0.10$). Whereby, excellent linearity of the output current from the oxygen pump element can be obtained over a wide range of the oxygen concentration, while allowing the output current to remain at a comparatively low level. To avoid deterioration of the response characteristics and difficulties in the manufacture, the minimum value of the spacing W is selected to be about 10 μm.

The open edge 2 should be provided along more than one quarter of the total periphery of the flat gap, preferably more than three quarters of the total periphery. With respect to the variation of oxygen concentration between the outside of the gap 1 and the deep inside portion of the gap 1, the open edge 2 should avoid any excessively localized restriction of oxygen diffusion which is experienced by conventional diffusion-restricting holes. Accordingly, the ratio of the total area Ae of the open edges 2 of the gap 1 to the surface area Z of the electrode 301 is, usually, considerably larger than a corresponding ratio in conventional lean burn type sensors having diffusion-restricting holes.

In the illustrated embodiment, suitable lead wires 6 connects the electrode layers 301 and 302 of the oxygen pump element to an outside power source 7 in such a manner that the outer electrode layer has a positive (+) potential relative to the other electrode layer 301, so that oxygen is pumped out from the gas in the gap 1. Before the oxygen pump element starts pumping, the gas inside the gap 1 has the same oxygen concentration as that of the outside gas whose oxygen concentration is to be measured. Since the spacing W is narrow, as the oxygen pump element pumps out the oxygen from the gap 1, an uneven distribution of oxygen concentration is caused in the gap 1, as shown in FIG. 3B. In the case of the illustrated embodiment of the invention, the oxygen partial pressure $PO_2$ decrease from the open edge toward the inside of the gap 1, as shown by the curve a of FIG. 3B. Thus, the restriction of the oxygen diffusion takes place not only at the open edges 2 but also within the gap 1. The distance or depth of that inside zone of the gap 1, which carries the electrode 301 and restricts the oxygen diffusion, can be given by a distance S from the edge of the electrode layer 301 to the point where the oxygen partial pressure $PO_2$ of the curve a assumes the minimum value. The depth S (to be referred to as the oxygen-diffusion-restricting zone depth, hereinafter) in the case of a rectangular electrode layer such as the illustrated electrode layer 301 becomes one half of the short side of such rectangular electrode layer 301. If the width of the short side of the rectangular electrode layer 301 is 2X, the oxygen-diffusion-restricting zone depth S becomes one half of 2X, i.e., S=X. The inventors have found that ratio of the spacing W of the flat gap 1 to the oxygen-diffusion-restricting zone depth S should preferably be less than 0.13, more preferably less than 0.10, as pointed out above. Accordingly, the oxygen partial pressure $PO_2$ in the gap 1, especially at the central portion of the gap 1, is reduced from that in the gas at the outside of the oxygen sensor. With the presence of a difference of the oxygen partial pressure $PO_2$ between the inside of the gap 1 and the outside of the oxygen sensor, an electromotive force is induced across the electrode layers 401 and 402 of the oxygen concentration cell element.

If the electric current through the oxygen pump element, i.e., the pumping current, is varied so as to maintain a constant level of the above-mentioned electromotive force across the oxygen concentration cell element, there will be a one-to-one (1:1) relationship between the pumping current and the oxygen concentration in the outside gas being measured, provided that the ambient temperature is substantially constant. Thus, it becomes possible to measure the oxygen concentration by using the pumping current. It is an important feature of the invention that a porous oxygen diffusion resistive layer is deposited at least on the gap side electrode layer of the oxygen pump element, so that excellent output characteristics such as a comparatively small pumping current and a high linearity can be obtained over a wide range of the oxygen concentration.

FIG. 4 shows a second embodiment of the oxygen sensor of the invention. In this embodiment, a paste consisting of major ingredient of heat resistive metallic material and ceramic material mixed therein is used to form a porous oxygen diffusion resistive layer which is to be deposited on at least the gap side surface of an oxygen-ion-conductive solid electrolyte board 3 of an oxygen pump element. After being applied on the surface of the board 3, the paste is sintered, so that a thick porous metallic layer 303 is formed, which layer 303 also acts as an electrode. In the embodiment of FIG. 4, the thick porous metallic layer 303 thus formed by a thick film forming method has a setback which is made by retarding the fringe of the layer 303 from the edge of the solid electrolyte board 3 by a distance l, but such setback can be dispensed with if so desired. The other electrode 304 to be deposited on the opposite surface of the solid electrolyte board 3 of the oxygen pump element in alignment with the gap side layer 303 can be a porous heat resistive metallic layer with a thickness of less than about 1 μm to be deposited by a thin film forming method. However, it is preferable to deposit a thick porous metallic layer 304, which is similar to the above-mentioned layer 303, to the outer surface of the solid electrolyte board 3, as shown in FIG. 4. Thereby, the electrode layer on the outer surface of the solid electrolyte board 3 is also provided with an oxygen diffusion resistive layer. Electrically insulating heat resistive material layers 330 and 340 are deposited on the setback portions adjacent to the electrodes 303 and 304 along the open edge 2 of the gap 1 by a thick film forming method.

The solid electrolyte board 4 of an oxygen concentration cell element is processed in a manner similar to the oxygen pump element board 3 and joined to the oxygen pump element so as to define a gap 1 therebetween. More particularly, thick porous metallic layers 403 and 404 are deposited on opposite surfaces of the solid electrolyte board 4 while leaving setbacks along the open edges 2 of the gap 1, by a thick film forming method. The setback portions are filled, for instance, by electrically insulating heat resistive layers 430 and 440 deposited thereon by a thick film forming method. Like parts as those of the first embodiment which has been described hereinbefore by referring to FIGS. 1 through 3 are designated by like numerals, and detailed description thereof is not repeated here.

In the oxygen sensor according to the present invention, the porous oxygen diffusion resistive layer to be deposited on or to be integral with the electrode layer should not be a mere thin layer with a thickness of about 1 μm made by depositing heat resistive metal through evaporation or plating, but such oxygen diffusion resistive layer should be a comparatively thick porous layers of electrically conductive or non-conductive type. The oxygen diffusion resistive layer to be used in the invention may be deposited by a thick film forming method in such a manner that it has an oxygen diffusion resistivity which is equivalent to that of a thick oxygen diffusion resistive layer having a thickness of 5–70 μm and a mean porosity of 10–40% as measured by using a porosimeter of pressurized mercury type.

As in the case of the first embodiment, the porous oxygen diffusion resistive layer to be deposited on the solid electrolyte board 3 of the oxygen pump element can be a combination of the porous electrode layer 301 and the porous electrode-covering layer 310. In this case, the layer acting as an electrode is a thick porous layer made of heat resistive metallic material such as platinum. A typical example of such combination consists a thin porous metallic layer with a thickness of 0.1–1 μm deposited by plating, sputtering, or evaporation, and a porous electrode-covering layer deposited on the metallic layer, which electrode-covering layer has a thickness of more than 5 μm and a porosity of 10–40%. The electrode-covering layer can be formed by powder metallurgy (sinter baking), by using a suitable adhesive for fixing the layer, or by plasma spray coating of suitable material such as metal, ceramics, or a suitable mixture or compound thereof.

Examples of the material of the electrode-covering layer are metals such as platinum (Pt), gold (Au), silver (Ag), palladium (Pd), and rhodium (Rh); oxides such as alumina, silica, mullite, spinel, and ferrite; carbides such as silicon carbide (SiC) and titanium carbide (TiC); nitride such as silicon nitride (SiN); adhesives such as silica ($SiO_2$) adhesive, alumina ($Al_2O_3$) adhesive and zirconia ($Zr_2O_3$) adhesive.

The porous oxygen diffusion resistive layer acting as an electrode, such as the porous metallic layer 303 or 304 of the second embodiment of FIG. 4, can be a sintered mixture of a heat resistive metallic material and a ceramic material. Examples of the metallic material for said porous oxygen diffusion resistive layer are platinum (Pt), an alloy of platinum and a platinum group metal, and other noble metals. Examples of the ceramic material for said porous oxygen diffusion resistive layer are electrically insulating metal oxides such as spinel and alumina; high electron-conductive metal oxides such as lanthanum calcium chromite, lanthanum strontium chromite, and lanthanum strontium cobaltite; and oxygen-ion-conductive solid electrolyte consisting of metal oxides. Preferably, the porous oxygen diffusion resistive layer should have a thickness of 5–70 μm and a mean porosity of 10–40%. Besides, the porous oxygen diffusion resistive layer may be made by other methods; for instance, a method consisting of steps of impregnating or plating electrode material in glass fibers or ceramic fibers, baking the fibers thus impregnated, and bonding the thus baked fibers onto an oxygen pump element, and another method consisting of steps of spreading a mixture of a spongy electrode material and a small amount of glass frit on an oxygen pump element, and then baking it.

The invention will be described in further detail by referring to Examples.

EXAMPLE 1

Specimen A of the oxygen sensor with the structure of the first embodiment of FIGS. 1 through 3 was prepared by making solid electrolyte boards 3 and 4 from sintered bodies of zirconia ($ZrO_2$) containing a 6 mole of yttria ($Y_2O_3$), each of the boards having a width of 12.4 mm, a length of 60 mm, and a thickness of 0.5 mm; depositing porous platinum electrodes 301, 302, 401, and 402 on the boards with the setback l of 1.2 mm, each of the electrodes having a thickness of 1 μm and an electrode area Z of 100 $mm^2$ (10 mm × 10 mm); depositing porous spinel electrode-covering layers 310, 320, 410, and 420, each of the electrode-covering layers having a thickness of 15 μm and a mean porosity of 20–30% as measured by a porosimeter; and bonding the two boards by a connecting member 5 made of a ceramic adhesive so that a gap 1 of the shape as shown in FIG. 1 with a gap spacing W of 0.25 mm was formed. Thus, the gap 1 of the Specimen A had a width of 12.4 mm, a depth of 11.2 mm, a spacing of 0.25 mm, and a total open edge area Ae of 8.7 $mm^2$ formed of the open edges 2 on the three sides thereof. The oxygen-diffusion-restricting zone depth S of the Specimen A proved to be 5 mm, so that the W/S ratio of the Specimen A was 0.05.

The operating characteristics of the Specimen A was measured as described hereinafter.

EXAMPLE 2

Specimen B of the oxygen sensor with the structure of the second embodiment of FIG. 4 was prepared by making solid electrolyte boards 3 and 4 from sintered bodies of the same material as those of the Specimen A, each of the boards having a width of 4 mm, a length of 60 mm, and a thickness of 0.5 mm; depositing porous thick metallic layers 303, 304, 403, and 404 on the boards with the setback l of 0.75 mm, each of the metallic layers having an electrode area Z of 18.8 $mm^2$ (with a width 2.5 mm and a length 7.5 mm), a thickness of 15 μm, and a mean porosity of 20–30%, the metallic layers being platinum porous layers containing 20% by weight of solid electrolyte oxides (zirconia $ZrO_2$ partially stabilized with yttria $Y_2O_3$) based on the weight of platinum; depositing porous spinel layers at the setbacks of the porous metallic layers as the heat resistive electric insulating layers 330, 340, 430, and 440; and bonding the two boards by a connecting member 5. Thus, the gap 1 of the Specimen B had a width of 4 mm, a depth of 8.3 mm, a spacing W of 0.08 mm, and a total open edge area Ae of 1.6 $mm^2$ formed of the open edges 2 on the three sides thereof. The oxygen-diffusion-restricting zone depth S of the Specimen B proved to be 1.25 mm, so that the W/S ratio of the Specimen B was 0.064.

The operating characteristics of the Specimen B was measured as described hereinafter.

EXAMPLE 3

Specimen C of the oxygen sensor with the structure of the second embodiment of FIG. 4 but different from the Specimen B was prepared. The only difference of the Specimen C from the Specimen B was in that the spacing W of the gap 1 was 0.16 mm. Thus, the gap 1 of the Specimen C had a total open edge area Ae of 3.2 $mm^2$ formed of the open edges 2 on the three sides thereof. The oxygen-diffusion-restricting zone depth S of the Specimen C proved to be 1.25 mm, so that the W/S ratio of the Specimen C was 0.13.

The operating characteristics of the Specimen B was measured as described hereinafter.

EXAMPLE 4

Reference Specimen D of an oxygen sensor whose structure fell outside the scope of the invention was prepared. The Reference Specimen D had a structure similar to that of the Specimen A but did not have any porous electrode-covering layers 310, 320, 410, and 420, so that the thin platinum electrode layers of the Reference Specimen D were bare.

The operating characteristics of the Reference Specimen D was measured as described hereinafter.

The relationship between the oxygen concentration of a gas being measured and the electric current through the oxygen pump element Ip for each of the above-mentioned Specimens A, B, C, and D was measured, under the condition that the output voltage of the oxygen concentration cell element was constant at 20 mV. The result is shown in FIG. 5.

MEASUREMENT 1

The response of each of the three Specimens of the oxygen sensor of the invention and one Reference Specimen was checked by the following method. Each Specimen was placed in a combustion duct, and propane gas was fed from the upstream of the combustion duct at a constant flow rate, so the propane gas was continuously burnt while supplying air thereto at a variable flow rate. The temperature of the burning gas was controlled at 500° C. by monitoring it with the indication of a thermometer, while the temperature of the oxygen sensor Specimen was held at 600°-700° C. by a sensor heater. At first, the air-fuel ratio λ of the fuel gas mixture was set at λ=1.00 (corresponding to an oxygen concentration of about 0%) by regulating the air flow. At the moment of 0.5 second after the start, the air-fuel ratio λ was suddenly changed to λ=1.20 (corresponding to an oxygen concentration of about 3.3%) by quick change of the air flow, and then the air-fuel ratio λ was readjusted to λ=1.00 at 0.5 second thereafter. Such sudden change and the readjustment of the air-fuel ratio λ was repeated and the instantaneous value of the output current Ip of each oxygen sensor Specimen was measured. During the tests, each oxygen sensor Specimen was connected to an electronic automatic voltage control circuit, which control circuit kept the output voltage Vs of the oxygen concentration cell element at a constant level by regulating the current Ip of the oxygen pump element thereof. The result of the measurement of the response is shown in Table 1.

TABLE 1

| Oxygen sensor Specimen | Response time (mS) |
|---|---|
| A | 150 |
| B | 70 |
| C | 150 |
| D | (more than 500) |

As can be seen from FIG. 5, the oxygen sensor of the present invention ensures stable measurement of the oxygen concentration with a smaller oxygen pump current Ip over a wide range of the oxygen concentration by the use of the porous oxygen diffusion resistive layers overlaid on the electrodes at least at the gap 1, as compared with the case without such oxygen diffusion resistive layers. The reason for such improvement appears to be as follows: namely, when such oxygen diffusion resistive layer is not overlaid on the electrode, the oxygen partial pressure $PO_2$ in the gap 1 is directly applied to the contact surface between the electrode and the solid electrolyte of the oxygen pump element. In the proximity of the open edge 2 where the distance from the outside is small, comparatively large oxygen partial pressure $PO_2$ close to the oxygen partial pressure $PO_2$ of the gas being measured directly reaches the above-mentioned contact surface. Accordingly, the pumping current Ip at such proximity of the open edge 2 increases much to a level which is restricted by the inner resistance of the solid electrolyte and the oxygen gas ionizing ability of the above-mentioned contact surface, so that the reducing effect of the oxygen partial pressure $PO_2$ due to the oxygen diffusion resistivity available at the gap 1 becomes rather inferior but the total pump current Ip becomes large. Namely, under the condition of a constant total pump current Ip (or constant power), the distribution of the oxygen partial pressure in the gap 1 becomes such that the oxygen partial pressure $PO_2$ at the central portion of the gap 1 in the case of without the oxygen diffusion resistive layer becomes larger than that with such oxygen diffusion resistive layer, as shown by the curve b of FIG. 3B.

On the other hand, when the porous oxygen diffusion resistive layer of the present invention is provided, the localized pumping current or localized rate of oxygen gas pumping in the proximity of the open edge 2, which is apt to be large in the prior art, is now restricted by the diffusion resistivity of the porous oxygen diffusion resistive layer. Accordingly, the oxygen partial pressure acting on the active surface (the contact surface between the solid electrolyte 3 and the electrode layer 301) of the electrode layer at such locality of the oxygen pump element is reduced as compared with that in the outside of the oxygen sensor, so that the counter electromotive force induced across the electrode layers of the oxygen pump element at such locality is considerably increased, so that the amount of oxygen gas being pumped at such locality is greatly restricted. Moreover, the oxygen gas pumping becomes more stable and more uniform over the electrode surface up to the central portion thereof, as compared with the prior art. Thus, the present invention produces an outstanding effect of considerably reducing the oxygen partial pressure $PO_2$ as compared with the prior art under the condition of a constant pumping current (or a contact power), as shown by the curve a of FIG. 3B. More particularly, the present invention facilitates the effective working of the diffusion restricting ability of the gap 1 over the entire span of the gap 1. It should be noted that in the oxygen sensor of the present invention, the effective working of the diffusion restricting ability over the entire span of the gap 1 does not cause any sacrifice in the response of the oxygen sensor, and the present invention actually improves the response as proved by the test result of Table 1.

Figure 6A:
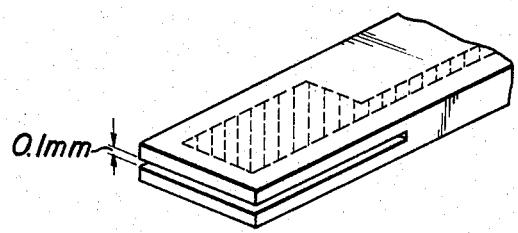
FIG. 6A is schematic perspective view of the Specimen of the oxygen sensor of the invention.
Figure 6B:
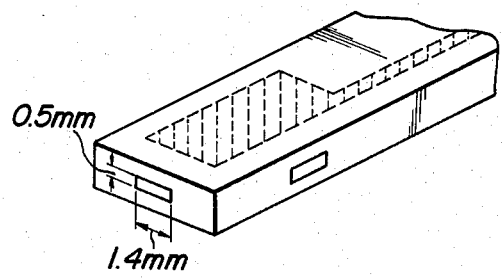
FIG. 6B and FIG. 6C are schematic perspective views of Reference Specimens which were tested together with the Specimens of the oxygen sensors of the invention.
Figure 6C:
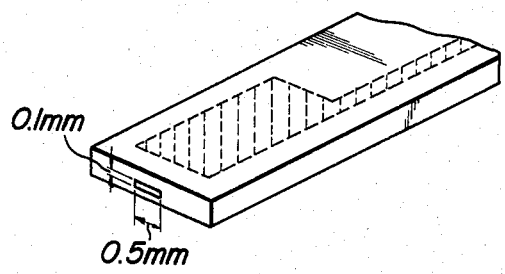

As compared with that oxygen sensors having restricting holes and enclosed chambers which oxygen sensors are out of the scope of the present invention, the oxygen sensor of the present invention provides response which is considerably improved as will be demonstrated hereinafter. More particularly, a Specimen E of the oxygen sensor of the invention as shown in FIG. 6A, two Reference Specimens F and G as shown in FIG. 6B and FIG. 6C were prepared.

The Specimen E of the invention was similar to the above-mentioned Specimen B except that the spacing W was 0.1 mm. Thus, the Specimen E had a total open edge area Ae of 2.1 mm² formed of the open edges 2 on the three sides thereof and a W/S ratio of 0.08.

The Reference Specimen F was prepared by making an oxygen sensor similar to the Specimen E with a gap spacing W of 0.5 mm; closing the open edges on the three sides of the gap 1 by attaching an end wall to the tip open edge and two sidewalls to the opposiste side open edges; boring three rectangular windows, one on the tip end wall and two on opposite sidewalls, each of which had a height of 0.5 mm and a width of 1.4 mm. Thus, the Reference Specimen F had a total open edge area Ae of 2.1 mm² formed of the three windows, and an enclosed chamber between the oxygen concentration cell element and the oxygen pump element which enclosed chamber communicated with the outside only through the above-mentioned three windows.

The Reference Specimen G was prepared by making an oxygen sensor similar to the Specimen E with a gap spacing W of 0.1 mm; closing the open edges on the three sides of the gap 1 by attaching an end wall to the tip open edge and two sidewalls to the opposite side open edges; boring only one rectangular window on the tip end wall, which window had a height of 0.1 mm and a width of 0.5 mm. Thus, the Reference Specimen F had a total open edge area Ae of 0.05 mm$^1$ formed of the single window, and an enclosed chamber between the oxygen concentration cell element and the oxygen pump element which enclosed chamber communicated with the outside only through the above-mentioned one window.

MEASUREMENT 2

The responses of the Specimen E of the oxygen sensor of the invention and the Reference Speciment F were checked by a method similar to the Measurement 1 except the following points. Namely, at first, the air-fuel ratio $\lambda$ of the fuel gas mixture was set at $\lambda = 1.00$ (corresponding to an oxygen concentration of about 0%) by regulating the air flow. At the moment of 0.5 second after the start, the air-fuel ratio $\lambda$ was suddenly changed to $\lambda = 1.18$ (corresponding to an oxygen concentration of about 3%), and then the air-fuel ratio $\lambda$ was readjusted to $\lambda = 1.00$ at 0.5 second thereafter. Such sudden change and the readjustment of the air-fuel ratio $\lambda$ was repeated, and the steady state value of the output current Ip of each oxygen sensor Specimen was measured together with its response time. During the tests, each oxygen sensor Specimen was connected to an electronic automatic voltage control circuit, which control circuit kept the output voltage Vs of the oxygen concentration cell element at a level of Vs=20 mV by regulating the current Ip of the oxygen pump element thereof. The result of the measurement of the response is shown in Table 2.

TABLE 2

| Oxygen sensor Specimen | Pump current Ip (mA) | | Response time (mS) | |
|---|---|---|---|---|
| | $\lambda = 1.00$ | $\lambda = 1.18$ | $\lambda = 1.00 \rightarrow$ 1.18 | $\lambda = 1.18 \rightarrow$ 1.00 |
| E (invention) | about 0.1 | about 20.1 | about 40 | about 60 |
| F (reference) | about 0.1 | about 19.8 | about 150 | about 55 |

MEASUREMENT 3

The responses of the Specimen E of the oxygen sensor of the invention and the Reference Specimen F were checked by a method similar to the Measurement 1 except the following points. Namely, at first, the air-fuel ratio $\lambda$ of th fuel gas mixture was set at $\lambda = 1.00$ (corresponding to an oxygen concentration of about 0%) by regulating the air flow. At the moment of 0.5 second after the start, the air-fuel ratio $\lambda$ was suddenly changed to $\lambda = 1.18$ (corresponding to an oxygen concentration of about 3%), and then the air-fuel ratio $\lambda$ was readjusted to $\lambda = 1.00$ at 0.5 second thereafter. Such sudden change and the readjustment of the air-fuel ratio $\lambda$ was repeated, and the steady state value of the output voltage Vs of the oxygen concentration cell element of each Specimen was measured together with its response time, while keeping the pumping current Ip of the oxygen pump element at a constant level of IP=20 mA. The result of the measurement of the response is shown in Table 3.

TABLE 3

| Oxygen sensor Specimen | Cell output Vs (mV) | | Response time (mS) | |
|---|---|---|---|---|
| | $\lambda = 1.00$ | $\lambda = 1.18$ | $\lambda = 1.00 \rightarrow$ 1.18 | $\lambda = 1.18 \rightarrow$ 1.00 |
| E (invention) | about 750 | about 20 | about 270 | about 300 |
| F (reference) | about 750 | about 20 | about 720 | about 290 |

MEASUREMENT 4

The response of the Specimen E of the oxygen sensor of the invention and the Reference Specimen G were checked by a method similar to the Measurement 1 except the following points. Namely, at first, the air-fuel ratio $\lambda$ of the fuel gas mixture was set at $\lambda = 1.05$ (corresponding to an oxygen concentration of about 0.8%) by regulating the air flow. At the moment of 0.5 second after the start, the air-fuel ratio $\lambda$ was suddenly changd to $\lambda = 1.15$ (corresponding to an oxygen concentration of about 2.5%), and then the air-fuel ratio $\lambda$ was readjusted to $\lambda = 1.05$ at 0.5 second thereafter. Such sudden change and the readjustment of the air-fuel ratio $\lambda$ was repeated, and the steady state value of the output voltage Vs of the oxygen concentration cell element of each Specimen was measured together with its response time, while keeping the pumping current Ip of the oxygen pump element at a certain constant level. The result of the measurement of the response is shown in Table 4.

TABLE 4

| Oxygen sensor Specimen | Pumping current Ip (mA) (constant) | Cell output Vs (mV) | | Response time (mS) | |
|---|---|---|---|---|---|
| | | $\lambda = 1.05$ | $\lambda = 1.15$ | $\lambda = 1.05 \rightarrow$ 1.15 | $\lambda = 1.15 \rightarrow$ 1.05 |
| E (invention) | 22.3 | 700 | 20 | about 350 | about 430 |
| G (reference) | 2.2 | 610 | 80 | about 1,150 | about 880 |

As can be seen from the result of the Measurements 2 through 4, the oxygen sensor of the invention showed quick response and excellent response balance between the response for oxygen concentration change from rich to lean and the response for oxygen concentration change from lean to rich, while the Reference Specimens of the out-of-invention structure showed inferior response than that of the present invention.

In the oxygen concentration cell element of the oxygen sensor of the invention, the area of the electrode on the side of the gap 1 may be reduced only to the proximity of the point where the oxygen partial pressure is most suppressed (i.e., the central portion of the gap 1). However, from the standpoint of the response, it is preferable to provide such electrode layer over the wide span of the gap-facing surface of the oxygen concentration cell element, which electrode layer has similar oxygen diffusion resistivity as that of the porous oxygen diffusion resistive layers of the oxygen pump element 3. The reason for it is in that the wide electrode layer acts to divert the current from the central portion of the gap 1, where localized high electromotive force is induced, toward the proximity of the open edges 2 where the local electromotive force is comparatively low, and such diversion of the current reduces the voltage drop due to the internal power loss within the oxygen concentration cell.

The configuration of the open edges 2 of the gap 1 of the oxygen sensor of the present invention is to be substantially free from localized suppression (choking) of the oxygen diffusion. Within this limit of the invention, it is possible to add for instance a few support members between the two cantilevered solid electrolyte boards 3 and 4 at the tip edge or the edge opposite to the connecting member 5, so as to improve the rigidity of the oxygen sensor, provided that such addition of the support member does not cause any substantial localized suppression of the oxygen diffusion.

As described in detail in the foregoing, the oxygen sensor of the invention has two solid electrolyte boards disposed face to face, and one of the boards is used as an oxygen concentration cell element, while the other one of the boards is used as an oxygen pump element, and a porous oxygen diffusion resistive layer is deposited on the surface of the oxygen pump element. As a result, a good linear relationship between the oxygen concentration of a gas being measured and the oxygen pumping current can be ensured with a comparatively small pumping current over a wide range of the oxygen concentration, for instance a pumping current of about 1–100 mA corresponding to a wide range of the oxygen concentration of about 0.1–10%. The configuration of the oxygen sensor of the invention facilitates accurate setting of the spacing W of the gap 1 with ease, so as to minimize dispersion in the quality of the products, and the wide openings of the gap 1 eliminates the risk of the fluctuation of the operating characteristics due to deposit of foreign matters. In short, the invention ensures excellent operating characteristics of the oxygen sensors.

It is noted that the illustrated embodiments of the oxygen sensor of the invention use mainly the oxygen pumping current as an indicator of the oxygen concentration of a gas, especially oxygen concentration of an exhaust gas, with a high sensitivity and a quick response, based on the relationship between the oxygen concentration of a gas being measured and a combination of the oxygen pumping current of the oxygen pump element and the output voltage of the oxygen concentration cell element. Instead of using the pumping current of the oxygen pump element as the indicator of the oxygen concentration under the condition of a constant output voltage of the oxygen concentration cell element, the output voltage of the oxygen concentration cell element may be used as the indicator of the oxygen concentration under the condition of the constant oxygen pumping current.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An oxygen sensor, comprising an oxygen pump element having a first oxygen-ion-conductive solid electrolyte board with electrode layers attached to opposite surfaces at one end of the first board, an oxygen concentration cell element having a second oxygen-ion-conductive solid electrolyte board with electrode layers attached to opposite surfaces at one end of the second board, a means for coupling said oxygen pump element and said oxygen concentration cell element in parallel to each other with a gap between the electrode layers attached to the opposing surfaces of the first board and the second board, and at least one oxygen diffusion resistive layer deposited on that electrode layer of said oxygen pump element which faces said gap, wherein said gap has a spacing W between opposing surfaces of said two elements, and said gap has an oxygen-diffusion-restricting zone depth S which is a distance from the edge of the electrode layer of the oxygen pump element in said gap to that point where the oxygen partial pressure is restricted to a minimum, said spacing W and said oxygen-diffusion-restricting zone depth S satisfying the condition of $(W/S)<0.13$, whereby said oxygen pump element transfers oxygen between said gap and the outside of said oxygen sensor therethrough under the presence of said oxygen diffusion resistive layer so as to produce such an oxygen concentration differential between said gap and the outside of the oxygen sensor that said oxygen concentration cell element generates an electomotive force in response to said oxygen concentration differential, a combination of an electric current and said electromotive force being indicative of oxygen concentration at the outside of the oxygen sensor.

2. An oxygen sensor as set forth in claim 1, wherein said gap has open edges extending along a part of periphery of the gap, total length of said open edges taken along the periphery of the gap being more than about one fourth of the total peripheral length of said gap.

3. An oxygen sensor as set forth in claim 1, wherein the surface of said oxygen pump element facing to said gap has a porous electrode-covering layer deposited thereon constituting said oxygen diffusion resistive layer.

4. An oxygen sensor as set forth in claim 1, wherein said oxygen diffusion resistive layer and said electrode on that surface of the oxygen pump element which faces said gap are formed as an integral porous metallic layer consisting of a main ingredient of heat resistive metallic material and ceramic material mixed therewith.

5. An oxygen sensor as set forth in claim 4, wherein said ceramic material is an electrically insulating metal oxide.

6. An oxygen sensor as set forth in claim 4, wherein said ceramic material is a metal oxide with a high electron conductivity.

7. An oxygen sensor as set forth in claim 4, wherein said ceramic material is a metal oxide with an oxygen-ion-conductivity.

8. An oxygen sensor as set forth in claim 1, wherein said gap has a spacing W between opposing surfaces of said two elements, and the electrode layer of the oxygen pump element in said gap has a width 2X between opposite open edges thereof, said spacing W and said width 2X satisfying a condition of $(W/X)<0.13$.

9. An oxygen sensor as set forth in claim 1, wherein said gap has a spacing W between opposing surfaces of said two elements, which spacing W is larger than 10 $\mu$m but smaller than 500 $\mu$m.

10. An oxygen sensor as set forth in claim 1, wherein said oxygen diffusion resistive layer is porous.

11. An oxygen sensor as set forth in claim 1, wherein said oxygen diffusion resistive layer has a resistance against oxygen diffusion, which resistance is similar to that of a metal oxide material with a thickness of 5–70 $\mu$m and a mean porosity of 10–40% as determined by a porosimeter of pressurized mercury type.

12. An oxygen sensor comprising an oxygen pump element having a first oxygen-ion-conductive solid electrolyte board with electrode layers attached to opposite surfaces at one end of the first board, and oxygen concentration cell element having a second oxygen-ion-conductive solid electrolyte board with electrode layers attached to opposite surfaces at one end of the second board, a means for coupling said oxygen pump element and said oxygen concentration cell element in parallel to each other with a gap between the electrode layers attached to the opposing surfaces of the first board and the second board, and at least one oxygen diffusion resistive layer deposited on that electrode layer of said oxygen pump element which faces said gap, wherein said gap has a spacing W between opposing surfaces of said two elements, and the electrode layer of the oxygen pump element in said gap has a width 2X between opposite open edges thereof, said spacing W and said width 2X satisfying the condition of $(W/X)<0.13$, whereby said oxygen pump element transfers oxygen between said gap and the outside of said oxygen sensor therethrough under the presence of said oxygen diffusion resistive layer so as to produce such an oxygen concentration differential between said gap and the outside of the oxygen sensor that said oxygen concentration cell element generates an electromotive force in response to said oxygen concentration differential, a combination of an electric current and said electromotive force being indicative of oxygen concentration at the outside of the oxygen sensor.

* * * * *